United States Patent
Ugajin et al.

(10) Patent No.: US 9,340,721 B2
(45) Date of Patent: May 17, 2016

(54) METHOD FOR PRODUCING OXIDIZABLE-METAL-CONTAINING COATING MATERIAL

(71) Applicant: KAO CORPORATION, Tokyo (JP)

(72) Inventors: Toru Ugajin, Utsunomiya (JP); Tetsuya Tabata, Haga-gun (JP); Yuki Kondo, Haga-gun (JP); Takahiro Maezawa, Haga-gun (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 14/352,626

(22) PCT Filed: Oct. 11, 2012

(86) PCT No.: PCT/JP2012/076286
§ 371 (c)(1),
(2) Date: Apr. 17, 2014

(87) PCT Pub. No.: WO2013/058159
PCT Pub. Date: Apr. 25, 2013

(65) Prior Publication Data
US 2014/0291577 A1    Oct. 2, 2014

(30) Foreign Application Priority Data

Oct. 18, 2011    (JP) .................................. 2011-228472
Sep. 21, 2012    (JP) .................................. 2012-208741

(51) Int. Cl.
*B05D 1/00*    (2006.01)
*C09K 5/16*    (2006.01)
(Continued)

(52) U.S. Cl.
CPC . *C09K 5/16* (2013.01); *B05C 5/005* (2013.01); *B05C 11/00* (2013.01); *C09D 7/14* (2013.01);
(Continued)

(58) Field of Classification Search
None
See application file for complete search history.

(56) References Cited

U.S. PATENT DOCUMENTS 6,056,822 A * 5/2000 Jefferson et al. .............. 118/683
6,436,128 B1   8/2002 Usui
(Continued)

FOREIGN PATENT DOCUMENTS

CN    1491271 A    4/2004
CN    1496395 A    5/2004
(Continued)

OTHER PUBLICATIONS

International Preliminary Report on Patentability, and Translation of Written Opinion of the International Searching Authority, dated Aug. 7, 2014, for International Application No. PCT/JP2012/076286 (Forms PCT/IB/338, PCT/IB/373 and PCT/ISA/237).
(Continued)

*Primary Examiner* — Nadine Norton
*Assistant Examiner* — Bradford Gates
(74) *Attorney, Agent, or Firm* — Birch, Stewart, Kolasch & Birch, LLP

(57) ABSTRACT

A method for producing a coated material having an oxidizable metal-containing coating, including the step of applying to a base material (11) an oxidizable metal-containing coating fluid containing a particulate oxidizable metal, a carbon component, a thickener, and water using a coating apparatus (1) and a coating fluid preparation step in which a thickener solution prepared by dissolving the thickener in water, the particulate oxidizable metal, and the carbon component or an aqueous dispersion of the carbon component are put and mixed in a preparation tank (3) to prepare the oxidizable metal-containing coating fluid. In the coating fluid preparation step, the particulate oxidizable metal is added to the thickener solution. The coating apparatus (1) includes a relay tank (4) capable of temporarily storing the coating fluid to be fed from the preparation tank (3) to a coating unit (5), so that the oxidizable metal-containing coating fluid in the preparation tank (3) is fed to the coating unit (5) through the relay tank (4).

15 Claims, 4 Drawing Sheets

(51) Int. Cl.
- *C09D 7/14* (2006.01)
- *B05C 11/00* (2006.01)
- *B05C 5/00* (2006.01)
- *D21H 23/48* (2006.01)
- *D21H 19/06* (2006.01)
- *C23C 26/00* (2006.01)
- *A61F 7/03* (2006.01)

(52) U.S. Cl.
CPC ............... *C23C 26/00* (2013.01); *D21H 19/06* (2013.01); *D21H 23/48* (2013.01); *A61F 7/034* (2013.01); *Y10T 428/31678* (2015.04)

(56) References Cited

U.S. PATENT DOCUMENTS

| | | | |
|---|---|---|---|
| 6,460,987 B1 * | 10/2002 | Katsuragi et al. | 347/100 |
| 2002/0151947 A1 | 10/2002 | Usui | |
| 2004/0042965 A1 | 3/2004 | Usui et al. | |
| 2004/0149732 A1 * | 8/2004 | Usui et al. | 219/528 |
| 2004/0217325 A1 | 11/2004 | Usui et al. | |
| 2009/0090346 A1 * | 4/2009 | Ajiri et al. | 126/204 |
| 2009/0101867 A1 | 4/2009 | Ishikawa et al. | |

FOREIGN PATENT DOCUMENTS

| | | |
|---|---|---|
| CN | 101233209 A | 7/2008 |
| JP | 5-208031 A | 8/1993 |
| JP | 11-89868 A | 4/1999 |
| JP | 11-155895 A | 6/1999 |
| JP | 11-299817 A | 11/1999 |
| JP | 2002-155273 A | 5/2002 |
| JP | 3344686 B2 | 11/2002 |
| JP | 2003-129041 A | 5/2003 |
| JP | 2003-336042 A | 11/2003 |
| JP | 2006-212115 A | 8/2006 |
| WO | WO 97/36968 A1 | 10/1997 |
| WO | WO 2007/078558 A1 | 7/2007 |
| WO | WO 2007/081014 A1 | 7/2007 |

OTHER PUBLICATIONS

PCT/ISA/210—International Search Report mailed on Jan. 8, 2013, issued in PCT/JP2012/076286.

Extended European Search Report, dated Jun. 25, 2015, for European Application No. 12841292.1.

* cited by examiner

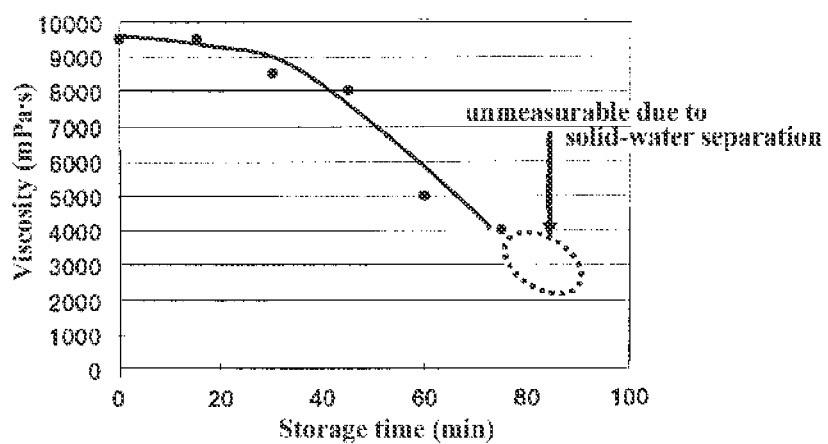

METHOD FOR PRODUCING OXIDIZABLE-METAL-CONTAINING COATING MATERIAL

TECHNICAL FIELD

The present invention relates to a method for producing a coated material having an oxidizable metal-containing coating as an intermediate product of a heat-generating element.

BACKGROUND ART

Conventional techniques for producing a heat-generating element that generates heat through reaction of an oxidizable metal with oxygen of air include, for example, the method for producing a heat generating element described in Patent Literature 1 below. This method includes applying an ink-like or creamy heat-generating composition to a base material sheet (covering material). The heat-generating composition is prepared by sequentially putting activated carbon, a thickener, a surfactant, a pH modifier, edible salt, and iron powder into a mixer in that order, stirring the mixture, and further kneading the mixture while adding water.

Patent Literature 2 below discloses a process for producing a heat-generating composition containing essentially iron powder, a carbon ingredient, a reaction accelerator, and water. The process includes providing a horizontal cylindrical mixer equipped with a rotatable screw, sequentially putting ingredients of the composition, such as iron powder and a carbon ingredient, in the cylindrical mixer and conveying the ingredients to a subsequent step while mixing by the rotation of the screw.

CITATION LIST

Patent Literature

Patent Literature 1: US 2002/0151947A1
Patent Literature 2: WO 2007/081014A1

SUMMARY OF INVENTION

Technical Problem

The heat generating composition prepared in a mixer by the technique of Patent Literature 1 lacks storage stability and is liable to inconvenience, such as large variation in viscosity with time and phase separation into solid and water. Additionally, the method of Patent Literature 1 is what we call a batchwise method, which is unsuited to continuous production, having difficulty in continuously transferring the heat generating composition as prepared to a subsequent step, e.g., of coating the heat generating composition to a base material, thus leaving room for improvement in production efficiency.

The technique of Patent Literature 2 is capable of feeding the heat-generating composition to a subsequent step in a continuous manner. However, because, when the production line is stopped, the ingredients being mixed up remain in the cylindrical mixer, resumption of the production line must be preceded by emptying the cylindrical mixer of the remaining contents. The emptying adds extra work to prepare the heat generating composition, and there is room for improvement in production efficiency all the same. Furthermore, since mixing and conveying the ingredients for making up the heat generating composition are conducted simultaneously in the cylindrical mixer, it is difficult to check the mixing state, which can result in adverse influence on the quality of the heat generating composition.

Solution to Problem

The invention provides a method for producing a coated material having an oxidizable metal-containing coating. The method includes the step of applying to a base material an oxidizable metal-containing coating fluid containing a particulate oxidizable metal, a carbon component, a thickener, and water using a coating apparatus including a preparation tank for preparing a coating fluid, a coating unit for applying the coating fluid to a base material to be coated, and transfer means connecting the preparation tank and the coating unit. The method includes a coating fluid preparation step in which a thickener solution prepared by dissolving the thickener in water, the particulate oxidizable metal, and the carbon component or an aqueous dispersion of the carbon component are put and mixed in the preparation tank to prepare the oxidizable metal-containing coating fluid. The coating fluid preparation step is carried out by adding the particulate oxidizable metal to the thickener solution. The coating apparatus further includes in its transfer means a relay tank capable of temporarily storing the coating fluid to be fed from the preparation tank to the coating unit, so that the oxidizable metal-containing coating fluid in the preparation tank is fed to the coating unit through the relay tank.

The invention also provides a method for producing a coated material having an oxidizable metal-containing coating. The method includes the step of applying to a base material an oxidizable metal-containing coating fluid containing a particulate oxidizable metal, a carbon component, a thickener, and water using a coating apparatus including a preparation tank for preparing a coating fluid, a coating unit for applying the coating fluid to a base material to be coated, and transfer means connecting the preparation tank and the coating unit. The method includes a coating fluid preparation step in which the thickener, the particulate oxidizable metal, and an aqueous dispersion of the carbon component are put and mixed in the preparation tank to prepare the oxidizable metal-containing coating fluid. The coating fluid preparation step is carried out by putting the aqueous dispersion of the carbon component and the thickener into the preparation tank and, after the thickener is dissolved in the aqueous dispersion of the carbon component, putting the particulate oxidizable metal in the preparation tank. The coating apparatus further includes in its transfer means a relay tank capable of temporarily storing the coating fluid to be fed from the preparation tank to the coating unit, so that the oxidizable metal-containing coating fluid in the preparation tank is fed to the coating unit through the relay tank.

The invention also provides a method for producing a heat-generating element including an electrolyte addition step in which an aqueous electrolyte solution containing an electrolyte is added to the coated material having an oxidizable metal-containing coating produced by the above described methods.

The invention also provides a method for producing a heat-generating element including an electrolyte addition step in which a solid electrolyte is added to the coated material having an oxidizable metal-containing coating produced by the above described methods.

Advantageous Effects of Invention

According to the invention, a coated material having an oxidizable metal-containing coating as a heat-generating element intermediate product is produced efficiently.

BRIEF DESCRIPTION OF DRAWINGS

FIG. 4($b$) is a graph showing change in viscosity of the coating fluid in the relay tank in Example 1.

FIG. 5 is a graph showing change in viscosity of the coating fluid in the preparation tank in Reference Example 1.

DESCRIPTION OF EMBODIMENTS

The invention relates to a method for producing a coated material having an oxidizable metal-containing coating, which method is capable of efficiently producing a heat-generating element intermediate product.

Figure 1:
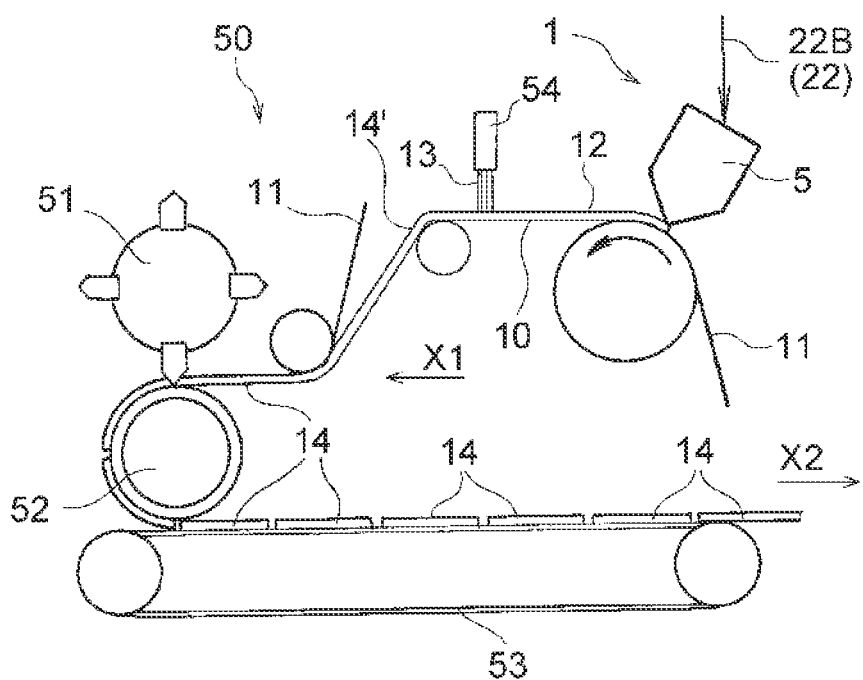
FIG. 1 is a schematic diagram showing a preferred embodiment of the method for producing a coated material having an oxidizable metal-containing coating, in which an oxidizable metal-containing coating fluid is applied to a base material.

A method for producing a coated material having an oxidizable metal-containing coating according to the invention (hereinafter also referred to simply as coated material) will be explained based on its preferred embodiments with reference to the accompanying drawings. A first embodiment of the invention provides a method for producing a coated material which, as shown in FIG. 1, produces a coated material 10, and includes the step of applying an oxidizable metal-containing coating fluid (hereinafter also referred to simply as coating fluid) to a base material 11 using a coating apparatus 1 (see FIG. 2) having a coating unit 5. In FIG. 1, reference numeral 12 indicates an oxidizable metal-containing layer formed by applying the coating fluid to the base material 11.

Figure 3:
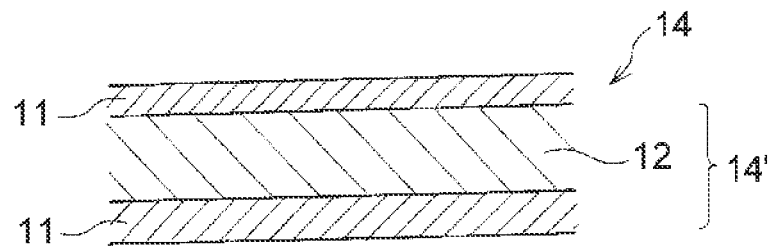
FIG. 3 is a schematic cross-section of a heat-generating element having the coated material with an oxidizable metal-containing coating as produced by the method shown in FIG. 1.

As shown in FIG. 1, the coating apparatus 1 is a part of a heat-generating element production apparatus 50 for making a heat-generating element 14 that generates heat on contact with air. The coated material 10 obtained by the method for producing a coated material according to the first embodiment is a sheet material composed of the base material 11 and the oxidizable metal-containing layer 12, which is an intermediate product of a heat-generating element 14 that utilizes heat generation accompanying oxidation reaction between oxygen in air and the oxidizable metal of the oxidizable metal-containing layer 12. As shown in FIG. 3, the heat generating element 14 is a three-layered flat sheet material having an upper and a lower base material 11 and the oxidizable metal-containing layer 12 interposed between the base materials 11. The heat generating element 14 includes the coated material 10 having a double layer structure composed of the lower base material 11 and the oxidizable metal-containing layer 12 formed by applying an oxidizable metal-containing coating fluid to the lower base material 11. As shown in FIG. 1, an aqueous electrolyte solution 13 containing an electrolyte or a solid-state electrolyte, a solid electrolyte 13 is then added to the oxidizable metal-containing layer 12 of the coated material 10 thereby to provide a heat-generating element 14' having a double layer structure. Another base material 11 is superposed on the oxidizable metal-containing layer 12 of the heat-generating element 14' to provide a desired product, a three-layered heat-generating element 14.

Figure 2:
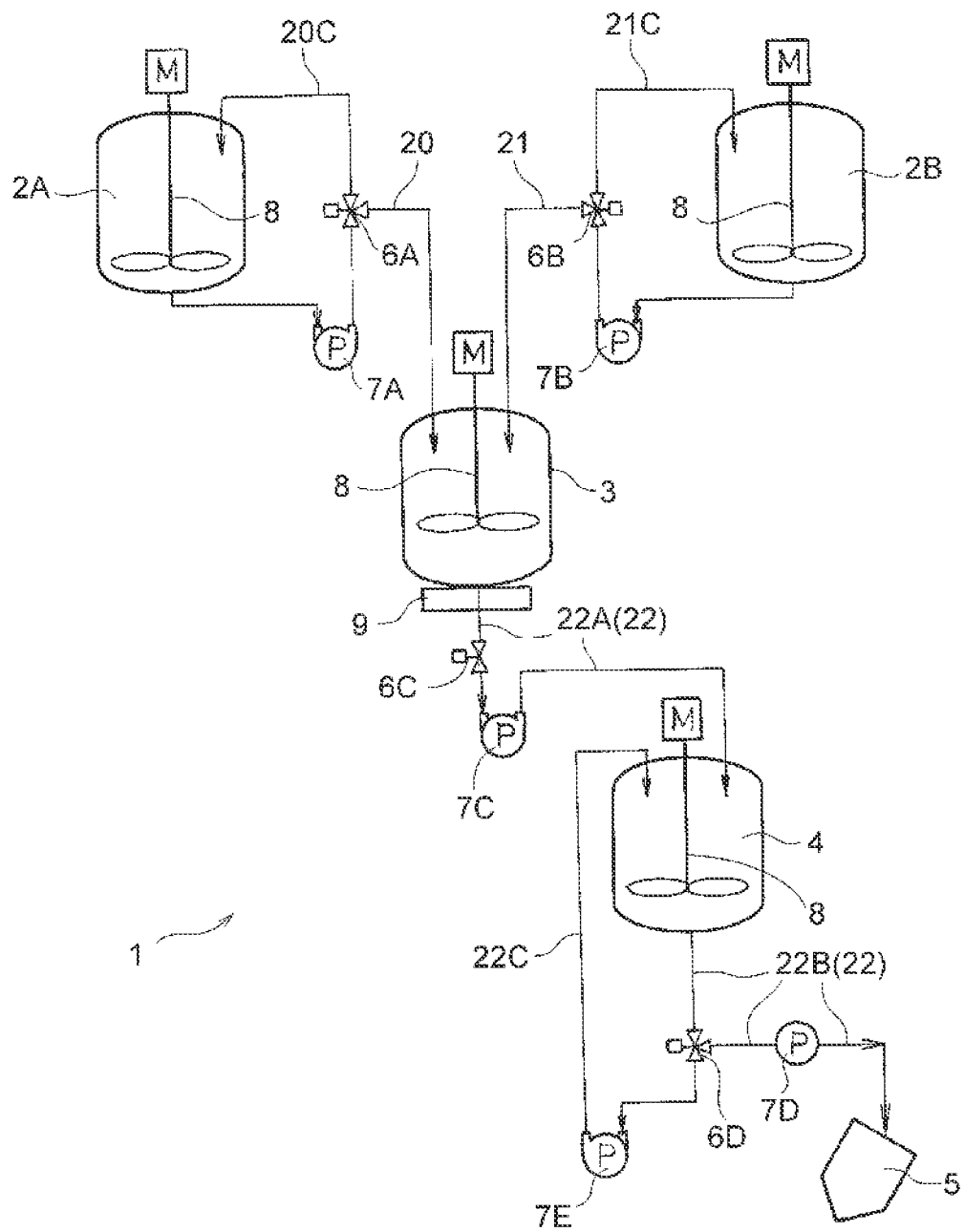
FIG. 2 is a simple configuration diagram of a coating apparatus having the coating unit shown in FIG. 1.

As shown in FIG. 2, the coating apparatus 1 includes a preparation tank 3 for preparing a coating fluid, a coating unit 5 for applying the coating fluid to the base material, and line 22 (pipe portions 22A and 22B) as transfer means for connecting the preparation tank 3 and the coating unit 5. The apparatus 1 further includes a preliminary preparation tank 2A connected to the preparation tank 3 through piping (a line 20 and a circulation line 20C hereinafter described) and a preliminary preparation tank 2B connected to the preparation tank 3 through piping (a line 21 and a circulation line 21C hereinafter described). The preliminary preparation tanks 2A and 2B are each used to prepare a liquid mixture by preliminarily mixing some of the components making up the coating fluid to be put in the preparation tank 3.

The preliminary preparation tank 2A is equipped with a circulation line 20C for circulating the fluid of the preliminary preparation tank 2A. The circulation line 20C is connected via a valve 6A to one end of the line 20 connecting with the preparation tank 3, so that the valve 6A switches back and forth between circulating the fluid of the preliminary preparation tank 2A using the circulation line 20C and feeding the fluid to the preparation tank 3. The circulation line 20C is equipped with a fluid delivery pump 7A by which the fluid in the preliminary preparation tank 2A is circulated in the circulation line 20C or fed to the preparation tank 3. The amount of the fluid fed to the preparation tank 3 is adjusted by the flow rate of the pump 7A.

The preliminary preparation tank 2B is equipped with a circulation line 21C for circulating the fluid of the preliminary preparation tank 2B. The circulation line 21C is connected via a valve 6B to one end of the line 21 connecting with the preparation tank 3, so that the valve 6B switches back and forth between circulating the fluid of the preliminary preparation tank 2B using the circulation line 21C and feeding the fluid to the preparation tank 3. The circulation line 21C is equipped with a fluid delivery pump 73 by which the fluid of the preliminary preparation tank 2B is circulated in the circulation line 21C or fed to the preparation tank 3. The amount of the fluid fed to the preparation tank 3 is adjusted by the flow rate of the pump 7B.

Whether the circulation lines 20C and 21C are used or not (whether the fluid is circulated or not) depends chiefly on the type of the fluids (components making up the coating fluid) to be sent from the preliminary preparation tanks 2A and 2B to the preparation tank 3. For example, in the case when settling of a component of the fluid is of concern, it is recommended to use the circulation line. More specifically, when, for example, the fluid sent from the preliminary preparation tank 2A (or 2B) to the preparation tank 3 is a thickener solution prepared by dissolving a thickener in water, it is unnecessary to use the circulation line 20C (or 21C), and when it is a liquid mixture of the thickener solution and a particulate oxidizable metal or an aqueous dispersion of a carbon component, because the particles of the oxidizable metal or the carbon component may settle out, it is preferred to operate the circulation line 20C (or 21C).

The preparation tank 3 has connected thereto the line 20 for receiving the fluid prepared in the preliminary preparation tank 2A, the line 21 for receiving the fluid prepared in the preliminary preparation tank 2B, and the line 22 (pipe portions 22A and 22B) for supplying the fluid (coating fluid) in the preparation tank 3 to the coating unit 5. As shown in FIG. 2, the preparation tank 3 is equipped with a metering device 9 for metering the amount of the raw materials of the coating fluid fed to the preparation tank 3. The amount of the fed raw materials is obtained from the change in mass or volume of the preparation tank 3 before and after the feed of the raw materials as measured with the metering device 9.

As shown in FIG. 2, the coating apparatus 1 used in the first embodiment has a relay tank 4 capable of temporarily storing the liquid (coating fluid) to be delivered from the preparation tank 3 to the coating unit 5. The relay tank 4 is located at the middle of the piping 22 connecting the preparation tank 3 and the coating unit 6 (in the transfer means connecting the preparation tank 3 and the coating unit 5). So, the coating fluid in the preparation tank 3 is adapted to be fed to the coating unit 5 through the relay tank 4.

The piping 22 has an upper pipe portion 22A connecting the preparation tank 3 and the relay tank 4 and a lower pipe portion 22B connecting the relay tank 4 and the coating unit 5. The upper pipe portion 22A has a valve 6C and a fluid delivery pump 7C. The liquid (coating fluid) in the preparation tank 3 is fed to the relay tank 4 by the pump 7C at a feed rate adjusted by the flow rate of the pump 7C. The lower pipe portion 22B has a valve 6D and a fluid delivery pump 7D. The liquid (coating fluid) in the relay tank 4 is fed to the coating unit 5 by the pump 7D at a feed rate adjusted by the flow rate of the pump 7D.

The relay tank 4 has a circulation line 22C for circulating the fluid of the relay tank 4. The circulation line 22C includes the valve 6D and part of the lower pipe portion 22B of the line 22 (the part upstream the valve 6D). The output flow of the fluid (coating fluid) from the relay tank 4 is chosen alternately between circulation through the circulation line 22C and feed to the coating unit 5 by switching the valve 6D. The circulation line 22C is equipped with a fluid delivery pump 7E, by which the fluid (coating fluid) in the relay tank 4 is circulated in the circulation line 22C.

Each of the preliminary tanks 2A and 2B, the preparation tank 3, and the relay tank 4 is not particularly limited in shape. Those used in the first embodiment have a cylindrical shape. These tanks are each equipped with a stirrer 8. The stirrers 8 are operated by their respective drive sources indicated by symbol M in FIG. 2 to agitate the fluid in the respective tanks. While depending on the ambient temperature of the coating apparatus 1, the fluid (coating fluid) can change in viscosity or form a precipitate. To prevent such a problem, it is preferred for the coating apparatus 1 to be equipped with a heater capable of heating the pipe portions of each of at least the circulation lines 20C, 21C, and 22C. From the same standpoint, it is also preferred for the coating apparatus 1 to be equipped with a heater capable of heating at least the preliminary' tanks 2A and 2B, the lines 20, 21, and 22, and the preparation tank 3.

The coating unit 5 may be any of known coaters, such as a die coater, a blade coater, an air knife coater, a roll coater, a bar coater, a gravure coater, a rod blade coater, lip coater, a curtain coater, and slide bead coater.

The coating fluid prepared and used in the method for producing a coated material according to the first embodiment, i.e., the oxidizable metal-containing coating fluid, will then be described. The coating fluid essentially contains a particulate oxidizable metal, a carbon component, a thickener, and water.

Examples of the oxidizable metal that can be used in the coating fluid include iron, aluminum, zinc, manganese, magnesium, and calcium. These metals may be used either individually or as a mixture thereof. Iron is preferred of them. The particle size of the particulate oxidizable metal is preferably 0.1 µm or greater, more preferably 5 µm or greater, and preferably 300 µm or smaller, more preferably 100 µm or smaller, even more preferably 50 µm or smaller, specifically preferably 0.1 to 300 urn, more preferably 5 to 100 µm, even more preferably 5 to 50 µm. As used herein, the term "particle size" denotes a median diameter measured in a wet system using a laser diffraction particle size distribution analyzer, SALD-300V from Shimadzu Corp.

The carbon component that can be used in the coating fluid has a function to accelerate oxidation reaction of the oxidizable metal with oxygen in air in the heat generating element 14 (see FIG. 1). It is preferred to use a carbon component having the function of a moisture retaining agent combined with the function of an oxygen retentive supplier. Examples of such a carbon component include activated carbon (e.g., palm shell charcoal, wood charcoal, bituminous coal, peat, and lignite), carbon black, acetylene black, and graphite. These components may be used either individually or as a mixture of two or more thereof. The carbon components described are usually particulate. The particle size of the carbon component is preferably 0.1 µm or greater, more preferably 1 µm or greater, and preferably 100 µm or smaller, more preferably 50 µm or smaller, even more preferably 30 µm or smaller. Specifically, the particle size is preferably 0.1 to 100 µm, more preferably 1 to 50 µm, even more preferably 1 to 30 µm. The "particle size" of the carbon component is a median diameter measured in a wet system using a laser diffraction particle size distribution analyzer, SALD-300V from Shimadzu Corp.

The thickener that can be used in the coating fluid is used mainly for the purpose of preventing settling of the particles of the oxidizable metal and imparting moderate flowability to the coating fluid. Examples of suitable thickeners include polymeric molding assistants of various types, such as celluloses, starches, poly(meth)acrylic acid salts or esters, syrups, agars, algae, plant mucilage substances, biological viscous materials, proteins, polysaccharides, and organic or inorganic synthetic polymers. They may be used either individually or as a mixture thereof. Preferred of them are polysaccharides. Xanthan gum is especially preferred in the invention. In the first embodiment, a solid (powdered) thickener is used as dissolved in water, and the resulting thickener solution is used to prepare the coating fluid according to feeding method A, B, or C hereinafter described.

If desired, the coating fluid may contain other components in addition to the aforementioned essential components (particulate oxidizable metal, carbon component, thickener, and water), such as a pH modifier, a surfactant, and a moisture retaining agent. The other components may be used individually or as a mixture thereof.

The pH modifier is added to one or more of the preliminary preparation tanks 2A and 2B and the preparation tank 3. The pH modifier to be added is an agent capable of adjusting the pH of the coating fluid or the liquid in the preliminary tank 2A or 2B to 10 or higher. The pH modifier to be added is selected as appropriate in the light of the extent of the influence on the main reaction, i.e., the oxidation reaction of the particulate oxidizable metal. Useful pH modifiers include weak acid salts and hydroxides of alkali metals or alkaline earth metals, such as potassium phosphates and sodium phosphates. Preferred pH modifiers include potassium phosphates, such as monopotassium phosphate, dipotassium phosphate, tripotassium phosphate, potassium pyrophosphate, potassium polyphosphate, and potassium metaphosphate. These pH modifiers can be used either individually or as a mixture thereof. These pH modifiers are generally solid (powder) at ambient temperature under ambient pressure.

Proportions of the components in the coating fluid are preferably selected as follows taking coating properties (fluidity) and heat generating performance into consideration.

The content of the particulate oxidizable metal is preferably 40 mass % or more, more preferably 50 mass % or more, and preferably 80 mass % or less, more preferably 70 mass % or less based on the total mass of the coating fluid. Specifically, it is preferably 40 to 80 mass %, more preferably 50 to 70 mass %.

The content of the carbon component is preferably 1 mass % or more, more preferably 3 mass % or more, and preferably 20 mass % or less, more preferably 10 mass % or less, specifically preferably 1 to 20 mass %, more preferably 3 to 10 mass %, based on the total mass of the coating fluid.

The content of the thickener is preferably 0.01 mass % or more, more preferably 0.05 mass % or more, and preferably 1 mass % or less, more preferably 0.30 mass % or less, specifically preferably 0.01 to 1 mass %, more preferably 0.05 to 0.30 mass %, based on the total mass of the coating fluid.

The content of water is preferably 10 mass % or more, more preferably 30 mass % or more, and preferably 60 mass % or less, more preferably 40 mass % or less, specifically preferably 10 to 60 mass %, more preferably 30 to 40 mass %, based on the total mass of the coating fluid.

A coating fluid containing metal particles having a large specific gravity like the coating fluid of the invention has poor storage stability. When, for example, such a coating fluid is prepared by the method described in Patent Literature 1 cited supra, that is, by sequentially putting the components (i.e., the particulate oxidizable metal, carbon component, thickener, and water) in a preparation tank and mixing by agitation, the resulting coating fluid has a decreasing viscosity with time due to, e.g., settling of the oxidizable metal particles, finally separating into solid matter and water. A coating fluid once having separated into solid matter and water is difficult to apply with known coating means, leading to difficulty in producing a coated material.

The inventors have conducted extensive studies on such a phase separation problem and found as a result that the main cause of the phase separation is adsorption of the dissolved thickener onto powder, especially the carbon component such as activated carbon, in the coating fluid. However, both the thickener causing the phase separation and the carbon component such as activated carbon should not be taken off the list of components of the coating fluid; the former being required for preventing the oxidizable metal particles from settling out, and the latter being required as a reaction accelerator in the heat generating element.

As a result of further study, the inventors have found that the coating fluid can be supplied to a subsequent processing step with stability by dividing the essential components of the coating fluid, i.e., the particulate oxidizable metal, carbon component, thickener, and water into three parts: (1) a thickener solution prepared by dissolving the thickener in water, (2) the particulate oxidizable metal, and (3) the carbon component or an aqueous dispersion of the carbon component, maintaining these parts stably, and feeding and mixing them together in a preparation tank to prepare the coating fluid before use. They have also found that it is effective in improving the storage stability of the coating fluid to put the oxidizable metal particles in the thickener solution but not in water.

The method for producing a coated material according to the first embodiment has been completed based on the above findings. One of the main characteristics of the method lies in that the method includes a coating fluid preparation step in which the three component parts discussed above are put and mixed in the preparation tank 3 of the coating apparatus 1 to prepare the coating fluid, the coating fluid preparation step being achieved by adding the particulate oxidizable metal to the thickener solution. The key points in the coating fluid preparation step of the first embodiment consist of (1) adding the thickener to the preparation tank 3 for preparing the coating fluid not in its solid state (powder) but in the form of a solution in water, (2) handling the carbon component and the thickener solution separately (avoiding mixing them) until addition to the preparation tank 3, and (3) adding the particulate oxidizable metal to the thickener solution (the thickener solution has been put in the preparation tank 3 by the time the particulate oxidizable metal is put in the preparation tank 3).

In carrying out the coating fluid preparation step of the first embodiment, there are three feed methods A to C for feeding the three divided parts of the components to the preparation tank, any one of which is chosen for preference. Feed methods A to C will be described in sequence. Description of methods B and C will generally be confined to the difference from method A. Otherwise, the discussion of method A appropriately applies to methods B and C.

Feed Method A:

In method A, the coating fluid preparation step is carried out by adding the particulate oxidizable metal to the thickener solution to prepare a liquid mixture beforehand, and putting the resulting liquid mixture and the aqueous dispersion of the carbon component in the preparation tank 3. This method is characterized by the two-liquid system of raw materials to be fed to the preparation tank 3: (1) a liquid mixture containing the particulate oxidizable metal, the thickener, and water and (2) the carbon component aqueous dispersion. Specifically, water and a thickener are poured in that order and mixed in the preliminary preparation tank 2A of the coating apparatus 1 while stirring by means of the stirrer 8 to prepare a thickener solution, to which the particulate oxidizable metal is added and mixed together to prepare a liquid mixture. By adding the particulate oxidizable metal to the thickener solution, the oxidizable metal particles in the resulting liquid mixture are effectively prevented from settling out as compared with, for example, adding water, the particulate oxidizable metal, and the thickener solution (or a solid thickener) in that order. The liquid mixture thus prepared in the preliminary preparation tank 2A is circulated through the circulation line 20C until use (until it is delivered to the preparation tank 3). To circulate the liquid mixture through circulation line 20C is effective in preventing the oxidizable metal particles from settling out.

The viscosity of the liquid mixture of the oxidizable metal particles and the thickener solution is preferably 1000 mPa·s or higher, more preferably 20000 mPa·s or higher, and preferably 100000 mPa·s or lower, more preferably 60000 mPa·s or lower, specifically preferably 1000 to 100000 mPa·s, more preferably 20000 to 60000 mPa·s, at 20° C. and 60% RH. The viscosity of the liquid mixture is adjustable by the kind or amount of the thickener as appropriate.

The viscosity of a liquid is measured as follows. In a beaker with an inner diameter of 60 mm is put 100 ml of a liquid under analysis (e.g., the above described liquid mixture or a coating fluid) and subjected to viscosity measurement using a Brookfield viscometer (available from Toki Sangyo Co., Ltd.). The measurement is carried out in an environment of 20° C. and 60% RH. A rotor No. 4 is rotated at 6 rpm, and the dial reading taken after one minute rotation is converted to a viscosity using a conversion chart.

The pH of the liquid mixture is preferably 10 or higher, more preferably 11 or higher, to prevent growth of bacteria and fungi. The pH of the liquid mixture is adjusted with the above-mentioned pH modifier. For example, water, the pH modifier, and the thickener are put and mixed in this order in the preliminary preparation tank 2A while stirring with the stirrer 8 to prepare a thickener solution, and the oxidizable metal is mixed into the thickener solution to prepare a liquid mixture having a pH within a predetermined range.

On the other hand an aqueous dispersion of a carbon component is prepared in the preliminary preparation tank 2B of the coating apparatus 1. Specifically, water, a powdered carbon component, such as activated carbon, are put and mixed in that order in the preliminary preparation tank 2B while stirring with the stirrer 8. The carbon component aqueous dispersion prepared in the preliminary preparation tank 2B is circulated through the circulation line 21C until use (until it is delivered to the preparation tank 3). Similarly to the liquid mixture, the pH of the carbon component aqueous dispersion is preferably 10 or higher, more preferably 11 or higher. The pH of the carbon component aqueous dispersion is adjusted with the above-mentioned pH modifier. For example, water, the pH modifier, and the carbon component are put and mixed in that order in the preliminary preparation tank 2B while stirring with the stirrer 8 to prepare a carbon component aqueous dispersion having a pH within a predetermined range.

A predetermined amount of the liquid mixture prepared in the preliminary preparation tank 2A and a predetermined amount of the carbon component aqueous dispersion prepared in the preliminary preparation tank 2B are fed to the preparation tank 3 while stirring with the stirrer 8 through the lines 20 and 21, respectively, and mixed to prepare a coating fluid. In method A, while the order of addition to the preparation tank 3 is not particularly limited, it is preferred in terms of mixing efficiency that addition of the carbon component aqueous dispersion with a smaller specific gravity be followed by the addition of the liquid mixture with a larger specific gravity.

The viscosity of the coating fluid is preferably 1000 mPa·s or more, more preferably 5000 mPa·s or more, and preferably 50000 mPa·s or less, more preferably 20000 mPa·s or less, specifically preferably 1000 to 50000 mPa·s, more preferably 5000 to 20000 mPa·s, at 20° C. and 60% RH in terms of stability of the coating step. The viscosity of the coating fluid can be adjusted appropriately by the type or amount of the thickener to be used.

To prevent growth of bacteria, and fungi, the coating fluid preferably has a pH of 10 or higher, more preferably 11 or higher. The pH of the coating fluid may be adjusted in the preferred range by previously adjusting the pH of every liquid used as a raw material of the coating fluid (all the liquids put in the preparation tank 3), i.e., the liquid mixture (thickener solution) and the carbon component aqueous dispersion preferably to 10 or higher, more preferably 11 or higher. Adjustment of the pH of every liquid used as a raw material of the coating fluid is achieved using the pH modifier as stated above.

Feed Method B:

In feed method B, the coating fluid preparation step is carried out by adding the thickener solution, the carbon component aqueous dispersion, and the particulate oxidizable metal to the preparation tank 3. While the order of putting the three parts in the preparation tank 3 is not particularly limited, the particulate oxidizable metal is preferably the last to be fed from the viewpoint of mixing efficiency. It does not matter which of the other two parts is fed first. The other two parts may be fed simultaneously. In method B, the usage of the coating apparatus 1 (preliminary preparation tanks 2A and 2B) is not particularly restricted. For example, the thickener solution and the carbon component aqueous dispersion may be prepared in the preliminary tanks 2A and 2B, respectively, and the solid oxidizable metal particles may be fed directly to the preparation tank 3 without using the preliminary preparation tank.

Feed Method C:

In feed method C, the coating fluid preparation step is carried out by adding the thickener solution, the carbon component, and the particulate oxidizable metal to the preparation tank 3. Method C is different from method B in that the carbon component is put in the preparation tank 3 not in the form of an aqueous dispersion but in the form of powder. That is, in the method for producing a coated material according to the invention, the carbon component may be fed to the preparation tank either as dispersed in water or in the form of powder. In method C, while the order of addition to the preparation tank 3 is not particularly limited, it is preferred in terms of mixing efficiency that the three components be added in the order of the thickener solution, the carbon component (powder), and the oxidizable metal particles. When method C is used, the usage of the coating apparatus 1 (preliminary preparation tanks 2A and 2B) is not particularly restricted. For example, the thickener solution may be prepared in the preliminary tank 2A, and the solid components, the carbon component and the oxidizable metal particles are fed directly to the preparation tank 3 without using the preliminary preparation tank.

The method for producing a coated material according to the first embodiment provides not only an improvement added to the manner of preparing a coating fluid (an oxidizable metal-containing coating fluid) but an improvement added to the manner of feeding the prepared coating fluid to a coating unit. As shown in FIG. 2, in the first embodiment, the coating fluid in the preparation tank 3 is once put in a relay tank 4 capable of temporarily storing the coating fluid and then fed to the coating unit 5.

Conventional coating apparatus of this type have a preparation tank for mixing raw materials to prepare a coating fluid directly connected by piping to a coating unit where the prepared coating fluid is used, the preparation tank serving as not only a coating fluid preparation tank but a coating fluid feed tank. Such a configuration has difficulty in flexibly and quickly responding to suspension of the production line or a continuous mode of coating fluid preparation, leaving room for improvement on production efficiency. When the production line using such a conventional configuration having a preparation tank and a coating unit directly connected to each other is suspended, the components being mixed remain in the preparation tank, resumption of the production line must be preceded by emptying the preparation tank of the remaining contents. The emptying adds extra work to produce a desired coated material, leaving room for improvement in production efficiency. Furthermore, since the coating fluid as used in the method of the first embodiment (i.e., an oxidizable metal-containing coating fluid) can decrease in viscosity with time on account of its poor storage stability as previously stated, it is desirable in terms of improvement on production efficiency to prepare the coating fluid immediately before use and to use up the prepared coating fluid in a relatively short time rather than to prepare a large volume of the coating fluid beforehand and to use the coating fluid little by little. Such desired usage of the coating fluid is difficult to accomplish with the conventional coating apparatus having a preparation tank and a coating unit directly connected to each other.

The above described problem associated with conventional coating apparatus (e.g., low production efficiency) is eliminated by providing the relay tank 4 into which the coating fluid of the preparation tank 3 is once stored and from which the coating fluid is fed to the coating unit 5 as in the first embodiment. By this configuration, the preparation tank 3 is specific as a coating fluid preparation tank, and the relay tank 4 is specific as a coating fluid feed tank. As a result, there is provided a coating method that is more suitable in handling an oxidizable metal-containing coating fluid having the poor storage stability problem, which method makes it feasible to stably and continuously produce a high quality coated material. As shown in FIG. 2, the relay tank 4 of the first embodiment is equipped with a circulation line 22C, in which the coating fluid fed from the preparation tank 3 may be circulated until use by the coating unit 5 and is thereby effectively prevented from changing in quality due to, e.g., settling of the oxidizable metal particles.

The feed of the coating fluid to the coating unit 5 by the use of the relay tank 4 can be carried out, for example, as follows. A predetermined amount (an amount that can be used up in a relatively short time of a coating fluid is prepared in the preparation tank 3 immediately before use of the coating fluid (immediately before applying the coating fluid to the base material 11 using the coating unit 5), and the prepared coating fluid is transferred to the relay tank 4 where it is temporarily stored while being fed to the coating unit 5. The coating unit 5 operates to sequentially apply the coating fluid fed from the relay tank 4 onto the base material 11. When the coating fluid runs low in the relay tank 4, a predetermined amount of the coating fluid is prepared again in the preparation tank 3 and supplied to the relay tank 4. This manner of coating fluid feed makes it possible to feed the coating unit 5 with a coating fluid always having the stable condition immediately after preparation, i.e., a coating fluid free of separation of solid from water, thereby facilitating; efficient, continuous, and stable production of a high quality coated material. With respect to the phrase "immediately before use of the coating fluid", the timing of starting the preparation of the coating fluid varies depending on the method of coating fluid preparation (the method of feeding the raw materials to the preparation tank), the configuration of the coating apparatus, and the like but is usually 1 to 180 minutes, preferably 1 to 60 minutes before the time when the coating fluid is applied to the base material for the first time.

The coating fluid fed to the coating unit 5 via the relay tank 4 is applied in a usual manner to one side of a continuous length of base material 11 being conveyed to form an oxidizable metal-containing layer 12 on that side of the base material 11. The amount of the coating fluid to be applied in terms of the weight of the oxidizable metal-containing layer 12 per unit area is preferably, but not particularly limited to, 100 g/m² or more, more preferably 500 g/m² or more, and preferably 5000 g/m² or less, more preferably 2500 g/m² or less, specifically preferably 100 to 5000 g/m², more preferably 500 to 2500 g/m², on a solid basis.

The mass (W) of the coating fluid prepared per unit time in the coating fluid preparation step is preferably not more than the product of the rate of consumption (V) of the coating fluid in the coating unit 5 and the pot life (usable time) (T) of the coating fluid, i.e., $W \leq V \times T$. The mass (W) of the coating fluid (oxidizable metal-containing coating fluid) prepared in the coating fluid preparation step is the mass of the coating fluid prepared per batch in the preparation tank 3, that is, the total mass of the raw materials (the oxidizable metal particles, the carbon component, the thickener, and water) as metered with the metering device 9 (see FIG. 2) attached to the preparation tank 3, which is equal to the mass of the coating fluid transferred from the preparation tank 3 to the relay tank 4 at a time.

The rate of consumption (V) of the coating fluid (oxidizable metal-containing coating fluid) is the mass of the coating fluid used by the coating unit 5 per unit time in the step of applying the coating fluid to the base material 11 (the step of producing a coated material 10), being expressed in mass per hour. The pot life (T) of the coating fluid (oxidizable metal-containing coating fluid) is the length of time from immediately after the preparation till when the coating fluid becomes difficult to apply, i.e., the length of time during which the coating fluid remains applicable. As previously noted, because the discussed type of coating fluid (oxidizable metal-containing coating fluid) is liable to separation of solid matter from water with time due to the presence of metal particles having a large specific gravity, it has a short pot life by its nature. As long as the relationship $W \leq V \times T$ is maintained, the coating fluid in the relay tank 4 remains usable in a continuous manner for a longer period of time without suffering phase separation, thereby providing a coating system more suited for industrial production.

The amount of an inventory buffer (B) of the relay tank 4 is preferably not less than the product of the sum (T3) of the time (T1) required for accomplishing the coating fluid preparation step and the transfer time (T2) required for transferring the prepared coating fluid to the relay tank 4 and the rate of consumption (V) of the coating fluid in the coating unit 5, i.e., $B \geq T3 (T1+T2) \times V$. The amount of an inventory buffer (B) of the relay tank is the minimum amount (mass) of the coating fluid stock in the relay tank 4 that is necessary for buffering. In other words, the amount of the buffer (B) is the minimum mass of the coating fluid required for smooth continuous operation of the production line including the coating apparatus 1. In the production line including the coating apparatus 1, the coating fluid is continuously used, while the coating fluid preparation in the preparation tank 3 is batchwise preparation. Buffering is necessary in order to perform continuous operation of such a hybrid production line having a batch system connecting with a continuous system. With the amount of the coating fluid in the relay tank 4 being less than the amount of the inventory buffer (B), the production line is not allowed to start, or if started, fails to achieve continuous operation. The time (T1) required for the coating fluid preparation step is the time required to supply all the necessary raw materials of the coating fluid (oxidizable metal particles, carbon component, thickener, and water) to the preparation tank 3, and to mix the raw materials by stirring to complete the coating fluid with a desired viscosity. To put it more specifically it is the length of time from immediately after issue of a command to prepare the coating fluid to the completion of the coating fluid in the preparation tank 3 (until immediately before the coating fluid in the preparation tank 3 is transferred to the next stage (relay tank 4)). The transfer time (T2) required for transferring the coating fluid (oxidizable metal-containing coating fluid) to the relay tank 4 is the length of time from immediately after completion of the preparation of the coating fluid in the preparation tank 3 to the completion of the transfer of the prepared coating fluid to the relay tank 4. The transfer time T2 is adjustable by appropriate condition setting of the liquid delivery pump 7C (see FIG. 2). The rate of consumption V is as defined above. As long as the relationship $B \geq T3 \times V$ is maintained, disadvantageous situations are more effectively prevented from arising where the relay tank 4 is emptied of the coating fluid and the production line must be stopped. As a result, the coating fluid remains usable in a continuous manner for a long period of time, whereby a coating system more suited for industrial production is provided.

The base material 11 is a sheet material on which the coating fluid (oxidizable metal-containing coating fluid) is applicable. A sheet material having bath water absorbing properties and surface smoothness is preferred. A water absorbing base material 11 will absorb the excess of water of the applied coating fluid (the oxidizable metal-containing layer 12) thereby to improve the heat generation characteristics of the resulting heat-generating element 14. Examples of suitable base materials 11 include paper made mainly of pulp fiber, and the like and obtained by a wet papermaking technique, a fiber sheet containing a superabsorbent polymer and pulp fiber, and nonwoven fabric made mainly of synthetic fiber. The basis weight of the base material 11 is not particularly limited and is preferably 30 g/m$^2$ or more, more preferably 80 g/m$^2$ or more, and preferably 200 g/m$^2$ or less, more preferably 120 g/m$^2$ or less, specifically preferably 30 to 200 g/m$^2$, more preferably 80 to 120 g/m$^2$.

The heat-generating element production apparatus 50 operates as follows. As shown in FIG. 1, the coating apparatus 1, specifically the coating unit 5 applies the coating fluid on one side of a continuous length of base material 11 to form an oxidizable metal-containing layer 12 to provide a continuous length of double-layered coated material 10 (a sheet having an oxidizable metal-containing coating). The continuous length of coated material 10 moves in the direction X1 indicated in FIG. 1 and is given an electrolyte on its side of the coating (the oxidizable metal-containing layer 12) by an electrolyte addition unit 54.

As shown in FIG. 1, the electrolyte addition unit 54 adds to the moving continuous length of coated material 10 an electrolyte aqueous solution 13 containing an electrolyte or an electrolyte in a solid form, i.e., a solid electrolyte 13 (an electrolyte addition step). Upon passing through the electrolyte addition step, the coated material 10 becomes a double-layered heat generating element 14' capable of heat generation on contact with air. The electrolyte aqueous solution or solid electrolyte functions as a catalyst for oxidation reaction between oxygen in air and the oxidizable metal in the double-layered heat generating element 14' for a three-layered heat generating element 14). The electrolyte aqueous solution is prepared by dissolving a solid electrolyte in water.

The electrolyte (solid electrolyte) that can be used here is capable of dissolving an oxide film formed on the oxidizable metal particles. Examples of such an electrolyte include sulfates, carbonates, chlorides, and hydroxides of alkali metals, alkaline earth metals, and transition metals. Preferred of them are chlorides of alkali metals, alkaline earth metals, or transition metals in view of their electroconductivity, chemical stability, and low production cost. Sodium chloride, potassium chloride, calcium chloride, magnesium chloride, ferrous chloride, and ferric chloride are especially preferred. The concentration of the electrolyte in the electrolyte aqueous solution is preferably at least 3 mass %, more preferably 5 mass % or more, and preferably 35 mass % or less, more preferably 30 mass % or less, specifically preferably 3 to 35 mass %, more preferably 5 to 30 mass %.

The electrolyte aqueous solution may be added by, for example, dropwise addition through nozzles, spraying using a spray, brush coating, or die coating. Dropwise addition through nozzles is preferred from the standpoint of preventing the electrolyte aqueous solution from splashing the surroundings or clogging the outlet for the solution. In the case where an electrolyte is added in a solid form, it is preferably added using a powder feeder. The amount of the electrolyte aqueous solution to be added is not particularly limited and is preferably 30 g/m$^2$ or more, more preferably 50 g/m$^2$ or more, and preferably 400 g/m$^2$ or less, more preferably 300 g/m$^2$ or less, specifically preferably 30 to 400 g/m$^2$, more preferably 50 to 300 g/m$^2$. The amount of the solid electrolyte to be added is not particularly limited and is preferably 1.5 g/m$^2$ or more, more preferably 2.5 g/m$^2$ or more, and preferably 20 g/m$^2$ or less, more preferably 15 g/m$^2$ or less, specifically preferably 1.5 to 20 g/m$^2$, more preferably 2.5 to 15 g/m$^2$.

In the heat-generating element production apparatus 50, another continuous length of base material 11 is laid on the oxidizable metal-containing layer 12 of the continuous length of double-layered heat generating element 14' coming from the electrolyte addition step to make a continuous length of three-layered heat generating element 14 as shown in FIG. 1. Then, the continuous length of heat generating element 14 passes between a cutter roller 51 having cutting blades on its periphery and an anvil roller 52 to be cut to length to give a plurality of heat generating elements 14. The resulting three-layered heat generating elements 14 are conveyed to direction X2 opposite to direction X1.

The thus obtained heat generating element 14 is used as, for example, a member constituting a heat-generating device (not shown). A heat generating device may be a device wearable on, for example, the loin or shoulder of a human body to accelerate systemic blood circulation or a device wearable on the eyes to induce a relaxed condition. A heat generating device usually has a flat shape composed of a pair of breathable sheets (not shown) and the heat generating element 14 sandwiched in between. The two breathable sheets provide a closed space in which the heat generating element 14 is placed.

A second embodiment of the method for producing a coated material having an oxidizable metal-containing coating will then be described. The description of the second embodiment will generally be confined to the difference from the first embodiment. Otherwise the description of the first embodiment applies appropriately to the second embodiment. The difference between the first and second embodiment resides in the coating fluid preparation step.

The inventors have studied on the phase separation of the coating fluid and found as a result that the coating fluid can be supplied to a subsequent processing step with stability by dividing the essential components of the coating fluid, i.e., the particulate oxidizable metal, carbon component, thickener, and water into three parts: (1) the thickener (in a solid (powdered) form), (2) the particulate oxidizable metal, and (3) an aqueous dispersion of the carbon component, maintaining these pans stably, and feeding and mixing them together in a preparation tank to prepare the coating fluid before use. They have also found that it is effective in improving the storage stability of the coating fluid to add the oxidizable metal particles to a thickened aqueous dispersion which is prepared by dissolving the thickener in the aqueous dispersion of the carbon component in the coating fluid preparation step.

The method for producing a coated material according to the second embodiment has been completed based on the above findings. One of the main characteristics of the method lies in that the method includes a coating fluid preparation step in which the three component parts discussed above are put and mixed in the preparation tank 3 of the coating apparatus 1 to prepare the coating fluid, the coating fluid preparation step being achieved by feeding the carbon component aqueous dispersion and the thickener to the preparation tank 3 before addition of the particulate oxidizable metal, and adding the particulate oxidizable metal to the preparation tank 3 after the thickener is dissolved in the carbon component aqueous dispersion. The key points in the coating fluid preparation step of the second embodiment consist of (1) adding the carbon component aqueous dispersion and the solid (powdered) thickener directly to the preparation tank 3 for preparing the coating fluid, followed by adding the oxidizable metal particles after the thickener is dissolved, and (2) handling the carbon component and the thickener separately (avoiding mixing them) until they are added to the preparation tank 3. In carrying out the coating fluid preparation step of the second embodiment, the three component parts are preferably put in the preparation tank 3 by feed method D described hereunder.

Feed Method D:

In feed method D, the coating fluid preparation step is carried out by adding the thickener, a carbon component aqueous dispersion, and the particulate oxidizable metal to the preparation tank 3. Feed method D is different from feed methods A, B, and C in that the thickener is added not in the form of a solution in a solvent but in a solid (powdered) form. That is, in the preparation of a coated material according to the invention, the thickener may be put in the preparation tank either as dissolved in water, i.e., in the form of a thickener solution as in the first embodiment or in the form of solid (powder) as in the second embodiment. In method D, it is preferred in terms of mixing efficiency that the component parts be added to the preparation tank 3 in the order of carbon component aqueous dispersion, solid (powdered) thickener, and particulate oxidizable metal and that the oxidizable metal particles be added after the thickener is dissolved in the previously added carbon component aqueous dispersion. In method D, the usage of the coating apparatus 1 (preliminary preparation tanks 2A and 2B) is not particularly restricted. For example, the carbon component aqueous dispersion may be prepared in the preliminary tank 2A or 2B, and the solid (powdered) thickener and the oxidizable metal particles may be fed directly to the preparation tank 3 without using the preliminary preparation tank.

While the invention has been described based on its preferred embodiments (the first and second embodiments), the invention is not limited thereto. For example, the configuration of the coating apparatus is not limited to that shown in FIG. 2, and a reservoir in which a liquid mixture prepared in the preliminary preparation tank is temporarily stored may be provided between the preliminary preparation tank 2A and the preparation tank 3 and between the preliminary preparation tank 2B and the preparation tank 3. While, in the aforementioned embodiments, the transfer means connecting the preparation tank and the coating unit is piping, the transfer means is not limited thereto. For example, the transfer means may be containerized transfer means or an automatic guided vehicle. In using containerized transfer means as means for connecting the preparation tank and the coating unit, the liquid in the preparation tank is transferred to the coating unit as contained in a portable container on a conveyor a conveyer belt) or by humans.

The numbers of the preliminary preparation tanks, relay tank, and coating unit constructing the coating apparatus are decided arbitrarily. For example, a plurality of relay tanks may be connected to a single preparation tank, one relay tank being connected to one coating unit. This configuration makes it feasible to operate a plurality of heat-generating element production lines at the same time. In this case, it is possible to produce different kinds of heat generating devices having different applications, for example, heat generating devices wearable on the skin and those wearable on the eyes.

With respect to the electrolyte addition step, while, in the foregoing embodiments, the electrolyte addition is carried out before the double layered coated material 10 composed of the base material 11 and the oxidizable metal-containing layer 12 is covered with another base material 11, the electrolyte may be added after another base material 11 is placed on the double-layered coated material 10, i.e., the electrolyte 110 may be added to the three-layered coated material 10. In the latter case, the electrolyte may be added to the three-layered coated material 10 either before or after the cutting to length with the cutter roller 51, i.e., to either the continuous length or cut sheet of the three-layered coated material 10.

In connection to the foregoing embodiments of the invention, the following clauses are further examples of the disclosed invention (the method for producing a coated material with an oxidizable metal-containing coating and the method for producing a heat generating element).

(1) A method for producing a coated material having an oxidizable metal-containing coating, comprising the step of applying to a base material an oxidizable metal-containing coating fluid containing a particulate oxidizable metal, a carbon component, a thickener, and water using a coating apparatus comprising a preparation tank for preparing the coating fluid, a coating unit for applying the coating fluid to the base material, and transfer means connecting the preparation tank and the coating unit, the method further comprising a coating fluid preparation step in which a thickener solution prepared by dissolving the thickener in water, the particulate oxidizable metal, and the carbon component or an aqueous dispersion of the carbon component are put and mixed in the preparation tank to prepare the oxidizable metal-containing coating fluid, the particulate oxidizable metal being added to the thickener solution in the coating fluid preparation step, the coating apparatus further comprising, in its transfer means, a relay tank capable of temporarily storing the coating fluid to be fed from the preparation tank to the coating unit, so that the oxidizable metal-containing coating fluid in the preparation tank is fed to the coating unit through the relay tank.

(2) The method as set forth in clause (1), wherein the coating fluid preparation step is carried out by previously adding the particulate oxidizable metal to the thickener solution to prepare a liquid mixture and putting the aqueous dispersion of the carbon component and the liquid mixture in the preparation tank, (3) The method as set forth in clause (2), wherein the aqueous dispersion of the carbon component and the liquid mixture are put in the preparation tank in that order.

(4) The method as set forth in clause (2) or (3), wherein the coating apparatus further includes a preliminary preparation tank for preparing the liquid mixture, the preliminary preparation tank being connected to the preparation tank by piping and equipped with a circulation line for circulating the liquid mixture in the preliminary preparation tank.

(5) The method as set forth in clause (1) wherein the coating fluid preparation step is carried out by putting the thickener solution, the aqueous dispersion of the carbon component, and the particulate oxidizable metal in the preparation tank.

(6) The method as set forth in clause (5), wherein the particulate oxidizable metal is the last to be put in the preparation tank.

(7) The method as set forth in clause (1), wherein the coating fluid preparation step is carried out by putting the thickener solution, the carbon component, and the particulate oxidizable metal in the preparation tank.

(8) The method as set forth in clause (7), wherein the thickener solution, the carbon component, and the particulate oxidizable metal are put in the preparation tank in that order.

(9) A method for producing a coated material having an oxidizable metal-containing coating, comprising the step of applying to a base material an oxidizable metal-containing coating fluid containing a particulate oxidizable metal, a carbon component, a thickener, and water using a coating apparatus comprising a preparation tank for preparing the coating fluid, a coating unit for applying the coating fluid to the base material, and transfer means connecting the preparation tank and the coating unit, the method further comprising a coating fluid preparation step in which the thickener, the particulate oxidizable metal, and an aqueous dispersion of the carbon component are put and mixed in the preparation tank to prepare the oxidizable metal-containing coating fluid, the coating fluid preparation step being carried out by putting the aqueous dispersion of the carbon component and the thickener in the preparation tank and then, after the thickener is dissolved in the aqueous dispersion of the carbon component, putting the particulate oxidizable metal in the preparation tank, the coating apparatus further comprising, in its transfer means, a relay tank capable of temporarily storing the coating fluid to be fed from the preparation tank to the coating unit, so that the oxidizable metal-containing coating fluid in the preparation tank is fed to the coating unit through the relay tank.

(10) The method as set forth in any one of clauses (1) to (9), wherein the mass of the oxidizable metal-containing coating fluid prepared per unit time in the coating fluid preparation step is not more than the product of the rate of consumption of the oxidizable metal-containing coating fluid in the coating unit and the pot life (usable time) of the oxidizable metal-containing coating fluid.

(11) The method as set forth in any one of clauses (1) to (10), wherein the amount of an inventory buffer of the relay tank is not less than the product of the sum of the time required for the coating fluid preparation step and the transfer time required for transferring the prepared coating fluid to the relay tank and the rate of consumption of the coating fluid in the coating unit.

(12) The method as set forth in any one of clauses (1) to (11), wherein the relay tank is equipped with a circulation line for circulating the coating fluid in the relay tank.

(13) The method as set forth in any one of clauses (1) to (12), wherein the oxidizable metal-containing coating fluid has a viscosity of from 1000 to 50000 mPa·s.

(14) The method as set forth in any one of clauses (1) to (13), wherein the oxidizable metal-containing coating fluid has a viscosity of from 0.5000 to 20000 mPa·s.

(15) The method as set forth in any one of clauses (1) to (14), wherein the oxidizable metal is at least one member selected from the group consisting of iron, aluminum, zinc, manganese, magnesium, and calcium.

(16) The method as set forth in any one of clauses (1) to (15), wherein the oxidizable metal is iron.

(17) The method as set forth in any one of clauses (1) to (16), wherein the particulate 110 oxidizable metal preferably has a particle size of 0.1 µm or greater, more preferably 5 µm or greater, and preferably 300 µm or smaller, more preferably 100 µm or smaller, even more preferably 50 µm or smaller, specifically preferably from 0.1 to 300 µm, more preferably from 5 to 100 µm, even more preferably 0.5 to 50 µm.

(18) The method as set forth in any one of clauses (1) to (16), wherein the carbon component is at least one member selected from the group consisting of activated carbon (e.g., palm shell charcoal, wood charcoal, bituminous coal, peat, and lignite), carbon black, acetylene black, and graphite.

(19) The method as set forth in any one of clauses (1) to (18), wherein the carbon component preferably has a particle size of 0.1 µm or greater, more preferably 1 µm or greater, and preferably 100 µm or smaller, more preferably 50 µm or smaller, even more preferably 30 µm or smaller, specifically preferably from 0.1 to 100 µm, more preferably 1 to 50 µm, even more preferably from 1 to 30 µm.

(20) The method as set forth in any one of clauses (1) to (19), wherein the thickener is at least one member selected from the group consisting of polymeric molding assistants of various types, such as celluloses, starches, poly(meth) acrylic acid salts or esters, syrups, agars, algae, plant mucilage substances, biological viscous materials, proteins, polysaccharides, and organic or inorganic synthetic polymers,

(21) The method as set forth in any one of clauses (1) to (20), wherein the thickener is of a polysaccharide type.

(22) The method as set forth in any one of clauses (1) to (21), wherein the thickener is xanthan gum.

(23) The method as set forth in any one of clauses (1) to (22), wherein the oxidizable metal-containing coating fluid has a pH of 10 or higher.

(24) The method as set forth in any one of clauses (1) to (23) wherein ever liquid used as a material of making the oxidizable metal-containing coating fluid has a pH of 10 or higher.

(25) The method as set forth in any one of clauses (1) to (24), wherein the oxidizable metal-containing coating fluid has a pH of 11 or higher.

(26) The method as set forth in any one of clauses (1) to (25), wherein every liquid used as a material of making the oxidizable metal-containing coating fluid has a pH of 11 or higher.

(27) The method as set forth in clause (24) or (26), wherein every liquid used as a material of making the oxidizable metal-containing coating fluid has its pH adjusted using a pH modifier.

(28) The method as set forth in any one of clauses (1) to (27), wherein the oxidizable metal-containing coating fluid further contains a pH modifier.

(29) The method as set forth in clause (27) or (28), wherein the pH modifier is at least one member selected from the group consisting of a weak acid salt and a hydroxide of an alkali metal and an alkaline earth metal.

(30) The method as set forth in any one of clauses (27) to (29), wherein the pH modifier is a potassium phosphate.

(31) The method as set forth in any one of clauses (27) to (30), wherein the pH modifier is tripotassium phosphate.

(32) A method for producing a heat-generating element comprising the step of adding an aqueous electrolyte solution containing an electrolyte to a coated material having an oxidizable metal-containing coating produced by the method set forth in any one of clauses (1) to (31).

(33) A method for producing a heat-generating element comprising the step of adding a solid electrolyte to a coated material having an oxidizable metal-containing coating produced by the method set forth in any one of clauses (1) to (31).

(34) The method as set forth in clause (33), wherein the solid electrolyte is added using a powder feeder.

(35) The method as set forth in any one of clauses (32) to (34), wherein the electrolyte is at least one member selected from the group consisting of a sulfate, a carbonate, a chloride, and a hydroxide of an alkali metal, an alkaline earth metal, and a transition metal.

(36) The method as set forth in any one of clauses (32) to (35), wherein the electrolyte is at least one member selected from the group consisting of an alkali metal chloride, an alkaline earth metal chloride, and a transition metal chloride.
(37) The method as set forth in any one of clauses (32) to (36), wherein the electrolyte is at least one member selected from the group consisting of sodium chloride, potassium chloride, calcium chloride, magnesium chloride, ferrous chloride, and ferric chloride.
(38) The method as set forth in any one of clauses (32) to (37), wherein the electrolyte is sodium chloride.

EXAMPLES

The invention will now be illustrated in greater detail with reference to Examples, but it should be understood that the scope of the invention is not limited thereto.

Example 1

A coating fluid (oxidizable metal-containing coating fluid) was applied to a base material to produce a coated material (a coated material having an oxidizable metal-containing coating) 10 of FIG. 1 using a coating apparatus having basically the same configuration of the coating apparatus 1 (see FIG. 2), The base material was a fibrous sheet containing a superabsorbent polymer and pulp fiber and having a basis weight of 100 g/m². The coating weight (the weight per unit area of the oxidizable metal-containing layer) was 2000 g/m² on a solid basis.

The coating fluid was prepared by feed method A. Specifically, water, a pH modifier, and a thickener were put in that order and mixed in the preliminary preparation tank 2A of the coating apparatus 1 shown in FIG. 2 to prepare a thickener solution. Oxidizable metal particles were added to and mixed with the thickener solution to prepare a liquid mixture, designated liquid A. Water, a pH modifier, and a powdered carbon component were put and mixed in the preliminary preparation tank 2B in that order to prepare a carbon component aqueous dispersion, designated liquid B. Liquids A and B were circulated until use (mixing) through the respective circulation lines including the preliminary tanks A and B, respectively. The circulation flow rate of liquid A was 6.5 kg/min, and that of liquid B was 2.5 kg/min. The compositions of liquids A and B are described below, Liquids A and B both had a pH of 11 or higher.
Composition of liquid A (liquid mixture of oxidizable metal particles and thickener solution): iron powder (RKH, particulate oxidizable metal, available from Iowa Electronics Materials Co., Ltd.; particle size: 50 μm) 73.2 mass %; thickener (Rhaball Gum GS-C, xanthan gum, from DSP Gokyo Food & Chemical Co., Ltd.) 0.2 mass %; pH modifier (tripotassium phosphate from Syowa Kosan Co., Ltd.) 1.0 mass %; water 25.6 mass %.
Composition of liquid B (carbon component aqueous dispersion): activated carbon as carbon component (Carboraffin from Japan EnviroChemicals, Ltd.; particle size: 45 μm) 20.3 mass %; pH modifier (tripotassium phosphate from Showa. Kosan) 3.6 mass %; water 76.1 mass %.

Immediately before use of a coating fluid (10 to 15 minutes before the time when a coating fluid is applied to the base material for the first time), liquid B and liquid A were put in the preparation tank 3 in that order and mixed to prepare a coating composition (oxidizable metal-containing coating fluid) with a pH of 11 or higher. The mixing ratio of liquid A to liquid B was 3.46:1 by mass. The coating fluid thus prepared in the preparation tank 3 was promptly transferred to the relay tank 4, in which the coating fluid was temporarily stored while being fed to the coating unit 5. When the coating fluid ran low in the relay tank 4, liquids A and B were mixed in the preparation tank 3 to prepare a predetermined amount of the coating fluid again and supplied to the coating unit 5 via the relay tank 4. The coating fluid was thus applied to the base material continuously by repeating the operation described above. During the continuous application of the coating fluid, a freshly prepared portion of the coating fluid was transferred to the relay tank 4 every 10 minutes. The composition of the coating fluid was as described below.
Composition of coating fluid: iron powder (RKH, particulate oxidizable metal, from Dowa. Electronics Materials Co., Ltd.; particle size: 50 μm) 56.8 mass %; activated carbon (carbon component, Carboraffin from Japan EnviroChemicals, Ltd.; particle size: 45 μm) 4.5 mass %; thickener (Rhaball Gum GS-C, xanthan gum, from DSP Gokyo Food & Chemical Co., Ltd.) 0.2 mass %; pH modifier (tripotassium phosphate from Syowa Kosan Co., Ltd.) 1.6 mass %; water 36.9 mass %.

Example 2

A coated material 10 shown in FIG. 1 (a coated material having an oxidizable metal-containing coating) was produced in the same manner as in Example 1, except that the coating fluid was prepared by feed method B. Specifically, water, a pH modifier, and a thickener were put in that order and mixed in the preliminary preparation tank 2A of the coating apparatus 1 shown in FIG. 2 to prepare a thickener solution. Water, a pH modifier, and a powdered carbon component were put and mixed in the preliminary preparation tank 2B in that order to prepare liquid B (the carbon component aqueous dispersion). Liquid B was circulated until use through the circulation line in the same manner as in Example 1. On the other hand, the thickener solution was stored in the preliminary preparation tank 2A until use without operating the circulation line. The thickener solution had a pH of 11 or higher. Immediately before using the coating fluid, liquid B, the thickener solution, and the oxidizable metal particles (iron powder with a particle size of 50 μm) were added in that order to the preparation tank 3. The mixing ratio of thickener solution:liquid B:oxidizable metal particles was 0.93:1.0:2.53 by mass. The composition of the thickener solution was as follows.
Composition of thickener solution: thickener (xanthan gum, Rhaball Gum GS-C, from DSP Gokyo Food & Chemical) 0.75 mass %; pH modifier (tripotassium phosphate from Showa Kosan) 3.73 mass %; water 95.52 mass %.

Example 3

A coated material 10 shown in FIG. 1 (a coated material having an oxidizable metal-containing coating) was produced in the same manner as in Example 1, except that the coating fluid was prepared by feed method D. Specifically, water, a pH modifier, and a powdered carbon component were put in that order and mixed in the preliminary preparation tank 2B of the coating apparatus 1 shown in FIG. 2 to prepare a carbon component aqueous dispersion, designated liquid C. Liquid C thus prepared was circulated until use (mixing) through the circulation line including the preliminary preparation tank 2B. The circulation flow rate of liquid C was 2.5 kg/min. The pH of liquid C was 11 or higher. Immediately before using the coating fluid, liquid C and a solid (powdered) thickener (Rhaball Gum GS-C, xanthan gum, from DSP Gokyo Food Chemical) were put and mixed in the preparation tank 3 in that order, followed by stirring with the stirrer 8 for 5 minutes to early out a thickener dissolving step. Thereafter, oxidizable metal particles (iron powder with a particle size of 50 m) were put in the preparation tank 3 and mixed. The mixing ratio of liquid C:solid (powdered) thickener:oxidizable metal particles was 71.8:0.25:100 by mass. The composition of liquid C was as follows.
Composition of liquid C (carbon component aqueous dispersion): activated carbon (carbon component) 10.19 mass %; pH modifier (tripotassium phosphate from Showa Kosan) 3.68 mass %; and water $6.13 mass %.

Reference Example 1

Figure 4A:
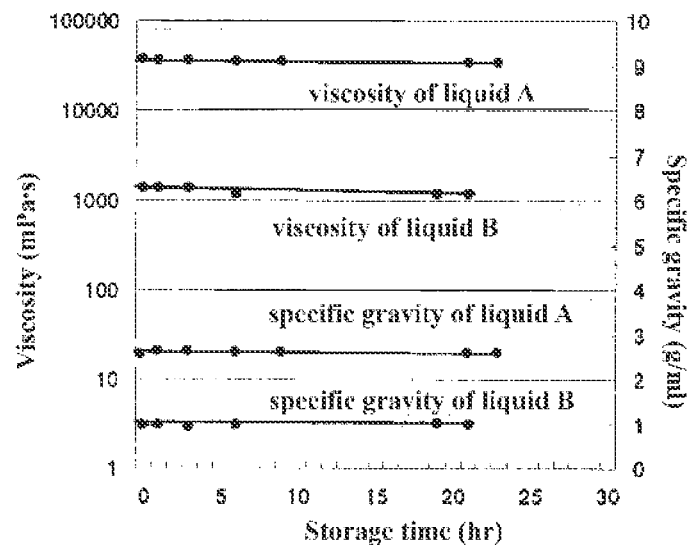
FIG. 4($a$) is a graph showing changes in viscosity and specific gravity of liquid A (a liquid mixture of a particulate oxidizable metal and a thickener solution) and liquid B (an aqueous dispersion of a carbon component) prepared in Example 1.
Figure 4B:
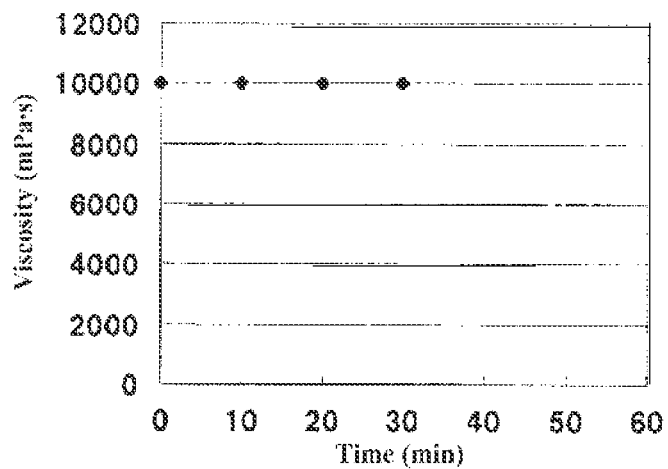

In a 200-liter preparation tank equipped with a circulation line were put iron powder, activated carbon, a thickener, a pH modifier, and water in the order of water, pH modifier, thickener, activated carbon, and iron powder and mixed to prepare a coating fluid (oxidizable metal-containing coating fluid) having the same composition as the coating fluid prepared in Example 1 and a pH of 11 or higher. The thus prepared coating fluid was stored while circulating through the circulation line at a circulation flow rate of 30 kg/min.
Evaluation:
The viscosity each of the liquids used in Example 1, i.e., liquid A (liquid mixture of oxidizable metal particles and a thickener solution), liquid B (carbon component aqueous dispersion) (liquids A and B being circulated in the respective circulation lines including the respective preliminary tanks), and the coating fluid in the relay tank was measured by the above described method at 20° C. and 60% RH at a predetermined interval to evaluate viscosity change with time. The specific gravity of liquids A and B was measured. The coating fluid prepared in Reference Example 1 which was circulated in the circulation line including the preparation tank was also evaluated for viscosity change with time in the same manner.
The liquids used in Examples 2 and 3 were evaluated in terms of viscosity change with time in the same manner as in Example 1. In Example 2, the thickener solution stored in the preliminary preparation tank, liquid B (carbon component aqueous dispersion) circulating in the circulation line including the preliminary preparation tank, and the coating fluid in the relay tank were each evaluated for changes in viscosity and pH with time. In Example 3, liquid C (carbon component aqueous dispersion) circulating in the circulation line including the preliminary preparation tank and the coating fluid in the relay tank were each evaluated for changes in viscosity and pH with time.
FIG. 4(*a*) is a graph showing changes in viscosity and specific gravity of liquid A (liquid mixture of oxidizable metal particles and a thickener solution) and liquid B (carbon component aqueous dispersion) prepared in Example 1. FIG. 4(*b*) is a graph showing change in viscosity of the coating fluid in the relay tank in Example 1. FIG. 5 is a graph showing change in viscosity of the coating fluid in the preparation tank in Reference Example 1. As is apparent from FIG. 4(*a*), liquids A and B of Example 1 both showed almost no change in viscosity even after the elapse of 20 hours. Noting that the change of specific gravity of the liquids provides an indication of separation of solid from water, liquids A and B of Example 1 both underwent almost no change in specific gravity with time, proving that the physical properties of the liquids were stable for a long period of time. As discussed earlier, the relay tank in Example 1 was replenished with the coating fluid freshly prepared in the preparation tank every 10 minutes. As is apparent from FIG. 4(*b*), the viscosity of the coating fluid stored in the relay tank in Example 1 was always stable during use of the coating fluid (while the coating fluid is fed from the relay tank to the coating unit), which state is less likely to cause a coating trouble.
While not graphically shown, the thickener solution and liquid B (carbon component aqueous dispersion) of Example 2 and liquid C (carbon component aqueous dispersion) of Example 3 were both underwent no change in viscosity and pH over 10 days. It was also confirmed that the coating fluid prepared from these liquids having 1.0 been stored 10 days had a desired viscosity and a pH of 11 or higher.
As is clear from FIG. 5, in contrast, the coating fluid of Reference Example 1 decreased in viscosity with time, and at last, after about 90 minutes from the preparation, separation of solid from water occurred, and the viscosity was no more measurable. FIG. 5 indicates that the pot life (usable time) of the coating fluid was about 60 minutes. From all these results, it has now been proved that the invention brings about improvement in storage stability of the coating fluid and every liquid material used to prepare the coating fluid (liquids A, B, and C and thickener solution) thereby making it feasible to efficiently produce a coated material with an oxidizable metal-containing coating.

The invention claimed is:
1. A method for producing a coated material having an oxidizable metal-containing coating, comprising the step of applying to a base material an oxidizable metal-containing coating fluid containing a particulate oxidizable metal, a carbon component, a thickener, and water using a coating apparatus comprising a preparation tank for preparing the coating fluid, a coating unit for applying the coating fluid to the base material, and transfer means connecting the preparation tank and the coating unit,
  the method further comprising a coating fluid preparation step in which a thickener solution prepared by dissolving the thickener in water, the particulate oxidizable metal, and the carbon component or an aqueous dispersion of the carbon component are put and mixed in the preparation tank to prepare the oxidizable metal-containing coating fluid, the particulate oxidizable metal being added to the thickener solution in the coating fluid preparation step,
  the coating apparatus further comprising, in its transfer means, a relay tank capable of temporarily storing the coating fluid to be fed from the preparation tank to the coating unit, so that the oxidizable metal-containing coating fluid in the preparation tank is fed to the coating unit through the relay tank.
2. The method according to claim 1, wherein the coating fluid preparation step is carried out by previously adding the particulate oxidizable metal to the thickener solution to prepare a liquid mixture, and putting the aqueous dispersion of the carbon component and the liquid mixture in the preparation tank.
3. The method according to claim 2, wherein the coating apparatus further comprises a preliminary preparation tank for preparing the liquid mixture, the preliminary preparation tank being connected to the preparation tank by piping and equipped with a circulation line for circulating the liquid mixture in the preliminary preparation tank.
4. The method according to claim 1, wherein the coating fluid preparation step is carried out by putting the thickener solution, the aqueous dispersion of the carbon component, and the particulate oxidizable metal in the preparation tank.
5. The method according to claim 1, wherein the coating fluid preparation step is carried out by putting the thickener solution, the carbon component, and the particulate oxidizable metal in the preparation tank.

6. The method according to claim 1, wherein the relay tank is equipped with a circulation line for circulating the coating fluid in the relay tank.

7. The method according to claim 1, wherein the oxidizable metal-containing coating fluid has a viscosity of from 1000 to 50000 mPa·s.

8. The method according to claim 1, wherein the amount of an inventory buffer of the relay tank is not less than the product of the sum of the time required for the coating fluid preparation step and the transfer time required for transferring the prepared coating fluid to the relay tank and the rate of consumption of the coating fluid in the coating unit.

9. The method according to claim 1, wherein the oxidizable metal-containing coating fluid has a pH of 10 or higher.

10. The method according to claim 1, wherein every liquid used as a material for preparing the oxidizable metal-containing coating fluid has a pH of 10 or higher.

11. The method according to claim 1, wherein the oxidizable metal-containing coating fluid further contains a pH modifier, the pH modifier being a potassium phosphate.

12. The method according to claim 1, wherein the oxidizable metal-containing coating fluid further contains a pH modifier, the pH modifier being tripotassium phosphate.

13. A method for producing a heat-generating element comprising the step of adding an aqueous electrolyte solution containing an electrolyte to a coated material having an oxidizable metal-containing coating produced by the method according to claim 1.

14. A method for producing a heat-generating element comprising the step of adding a solid electrolyte to a coated material having an oxidizable metal-containing coating produced by the method according to claim 1.

15. A method for producing a coated material having an oxidizable metal-containing coating, comprising the step of applying to a base material an oxidizable metal-containing coating fluid containing a particulate oxidizable metal, a carbon component, a thickener, and water using a coating apparatus comprising a preparation tank for preparing the coating fluid, a coating unit for applying the coating fluid to the base material, and transfer means connecting the preparation tank and the coating unit, the method further comprising a coating fluid preparation step in which a thickener solution prepared by dissolving the thickener in water, the particulate oxidizable metal, and the carbon component or an aqueous dispersion of the carbon component are put and mixed in the preparation tank to prepare the oxidizable metal-containing coating fluid, the particulate oxidizable metal being added to the thickener solution in the coating fluid preparation step, the coating apparatus further comprising, in its transfer means, a relay tank capable of temporarily storing the coating fluid to be fed from the preparation tank to the coating unit, so that the oxidizable metal-containing coating fluid in the preparation tank is fed to the coating unit through the relay tank, and wherein the mass of the oxidizable metal-containing coating fluid prepared per unit time in the coating fluid preparation step is not more than the product of the rate of consumption of the oxidizable metal-containing coating fluid in the coating unit and the pot life of the oxidizable metal-containing coating fluid.

* * * * *